United States Patent
Busiashvili

(10) Patent No.: US 12,089,957 B1
(45) Date of Patent: *Sep. 17, 2024

(54) VEHICLE DIAGNOSTIC SYSTEM FOR DETECTING HEARTBEAT FREQUENCY USING STEERING WHEEL PHOTOPLETHYSMOGRAPHY SENSOR

(71) Applicant: Stat Capsule Inc., Glendale, CA (US)

(72) Inventor: Yuri Busiashvili, Los Angeles, CA (US)

(73) Assignee: Stat Capsule Inc., Glendale, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 18/485,408

(22) Filed: Oct. 12, 2023

Related U.S. Application Data

(63) Continuation-in-part of application No. 18/183,573, filed on Mar. 14, 2023, now Pat. No. 11,820,384.

(51) Int. Cl.
- *A61B 5/00* (2006.01)
- *A61B 5/024* (2006.01)
- *B60Q 1/50* (2006.01)
- *B60W 30/08* (2012.01)

(52) U.S. Cl.
CPC ........ *A61B 5/6893* (2013.01); *A61B 5/02427* (2013.01); *B60Q 1/544* (2022.05); *B60W 30/08* (2013.01); *B60W 2540/221* (2020.02)

(58) Field of Classification Search
None
See application file for complete search history.

(56) References Cited

U.S. PATENT DOCUMENTS

| | | | |
|---|---|---|---|
| 5,769,085 | A | 6/1998 | Kawakami et al. |
| 6,822,573 | B2 | 11/2004 | Basir et al. |
| 7,397,382 | B2 | 7/2008 | Ikegami et al. |
| 8,106,783 | B2 | 1/2012 | Wada et al. |
| 9,124,955 | B2 | 9/2015 | Geva et al. |
| 9,409,517 | B2 | 8/2016 | Han et al. |

(Continued)

FOREIGN PATENT DOCUMENTS

WO    2019027389    2/2019

OTHER PUBLICATIONS

Purnamasari et al., "Heart Beat Based Drowsiness Detection System for Driver", 2018 International Seminar on Application for Technology of Information and Communication (iSemantic), pp. 585-590 (Year: 2018).*

(Continued)

*Primary Examiner* — Tamara L Weber
(74) *Attorney, Agent, or Firm* — Ralph D Chabot

(57) ABSTRACT

A vehicle equipped with a computer system capable of diagnosing a pulseless condition in the driver. The vehicle includes a steering wheel with photoplethysmography sensors positioned around its circumference to measure arteriolo-capillary pulse wave intervals when the driver grips the steering wheel. The computer system is connected to the steering wheel sensors, a proximity sensor system, rear tail lights, a navigation system, and an audio system. The computer system analyzes the time interval between consecutive arteriolo-capillary pulse waves and determines if it (Continued)

exceeds a predetermined time interval. If the predetermined time interval is exceeded, the computer system will perform steps for the safety of the driver.

3 Claims, 2 Drawing Sheets

(56) References Cited

U.S. PATENT DOCUMENTS

| | | | |
|---|---|---|---|
| 9,855,945 | B2 | 1/2018 | Fung et al. |
| 9,993,191 | B2 | 6/2018 | Lian |
| 10,015,649 | B2 | 7/2018 | Ulmansky et al. |
| 11,331,025 | B2 | 5/2022 | Yoon et al. |
| 2008/0143504 | A1 | 6/2008 | Martin Alvarez |
| 2009/0209829 | A1 | 8/2009 | Yanagidaira et al. |
| 2010/0130808 | A1 | 5/2010 | Hattori |
| 2010/0295707 | A1 | 11/2010 | Bennie et al. |
| 2014/0275834 | A1 | 9/2014 | Bennett |
| 2016/0001781 | A1 | 1/2016 | Fung |
| 2018/0348759 | A1 | 12/2018 | Freeman |
| 2019/0139411 | A1 | 5/2019 | Dhull |
| 2019/0202467 | A1 | 7/2019 | Sun |
| 2019/0276033 | A1* | 9/2019 | Fung .................. G06V 10/764 |
| 2019/0316922 | A1 | 10/2019 | Petersen |
| 2019/0382025 | A1* | 12/2019 | Mena Benito ........... A61B 5/18 |
| 2020/0156648 | A1* | 5/2020 | Zhang .................. B60W 40/08 |
| 2020/0317210 | A1* | 10/2020 | Yang .................... B60W 50/14 |
| 2020/0342756 | A1 | 10/2020 | MacKenzie |
| 2020/0383580 | A1 | 12/2020 | Shouldice et al. |
| 2021/0016805 | A1 | 1/2021 | Oba et al. |
| 2021/0232901 | A1 | 7/2021 | Rundo |
| 2022/0153302 | A1* | 5/2022 | Arechiga-Gonzalez .................... A61B 5/7264 |
| 2022/0164026 | A1 | 5/2022 | Sicconi et al. |
| 2022/0402502 | A1 | 12/2022 | Neagu Chivu |

OTHER PUBLICATIONS

Branko Babusiak, Adrian Hajducik, Stefan Medvecky, Michal Lukac, Jaromir Klarak, Design of Smart Steering Wheel for Unobtrusive Health and Drowsiness Monitoring, Aug. 5, 2021.

* cited by examiner

VEHICLE DIAGNOSTIC SYSTEM FOR DETECTING HEARTBEAT FREQUENCY USING STEERING WHEEL PHOTOPLETHYSMOGRAPHY SENSOR

BACKGROUND OF THE INVENTION

Life begins with the first heart beat, or first spark; an electrical signal generated in the heart that travels through the conduction system and activates the heart muscle. This is an electro-mechanical event called cardiac cycle. The heart does not stop throughout the life cycle. Towards the seventh to eighth decade of life, the generator of this electrical spark, a natural pacemaker, in some individuals does not function as reliably as earlier in life. This lack of reliable function can be sick sinus syndrome, or an electrical impulse gets stuck in the conductive system, the condition called atrioventricular block. In these conditions, the heart muscle doesn't activate and the heart goes silent. Most of the time, the natural pacemaker will recover its function within seconds spontaneously. If not, the affected heart goes "silent", a condition called cardiac standstill. If cardiac silence and no pulse condition extends beyond 7-10 seconds, an individual loses consciousness.

If cardiac standstill continues for over 10-15 seconds, it is termed cardiac arrest. The odds of re-starting the electro-mechanical heart activity diminish with every subsequent second of cardiac silence, or standstill. The American Heart Association (AHA) recommends implantation of electronic pacemaker if the cardiac silence is documented to exceed 3 seconds.

The pause, or electro-mechanical silence has to be identified. For this purpose, there are cardiac monitors that are used for days and weeks to identify potential candidates for an artificial pacemaker. Electrical activity of the heart is monitored; no electrical activity translates into no mechanical contraction. Mechanical activity usually is monitored in a hospital setting where activity can be monitored by arterial line; directly reflecting arterial blood pressure fluctuations.

The heart conditions mentioned earlier can manifest itself in situations most dangerous to the individual. One of these situations can occur when a driver of a vehicle suffers a cardiac arrest.

For example, cardiac conditions such as a pulseless condition, Brady-arrhythmia or tachyarrhythmia can be experienced by an elderly driver and can easily go undetected. These types of cardiac conditions can potentially result in full cardiac arrest which can be a life-threatening situation to both the driver as well as other people in proximity; particularly if the driver were to lose the mental and physical capability to control the vehicle.

Many modern vehicles are equipped with technology including a computer, proximity sensor systems, cameras, heads-up display (HUD) and mobile GPS navigation which can allow a vehicle so equipped to be controlled by the computer based on information it receives regarding the vehicle location, speed and proximity of nearby objects.

Photoplethysmography (PPG) is an uncomplicated and inexpensive optical measurement method that is often used for heart rate monitoring purposes. It is also a modality that can detect the loss of a mechanical pulse wave and is a good indicator of a pulseless condition. PPG sensors have been widely used in many types of devices such as attachments to ear lobes and fitness style watches.

A pulseless condition can lead to full cardiac arrest. After the heart goes "silent" for a few cardiac cycles, peripheral blood flow in the brain drops to zero and the individual loses conscience usually after about 6-7 seconds or 6-7 missed cardiac cycles.

Previous approaches for diagnosing pulseless conditions in drivers of vehicles have primarily relied on external monitoring devices, such as wearable heart rate monitors or pulse oximeters, which are not integrated into the vehicle itself. These external devices typically require the driver to wear a sensor on their body, which can be inconvenient and uncomfortable. Additionally, these devices may not provide real-time monitoring or immediate notification to the driver in the event of a pulseless condition.

Some prior art systems have attempted to integrate pulse monitoring sensors into the steering wheel of a vehicle. These systems typically use electrodes to measure the driver's pulse. However, these contact-based sensors can be unreliable.

However, none of these approaches have provided a comprehensive solution that combines the features described in this disclosure. The present invention addresses the limitations of previous approaches by integrating photoplethysmography sensors directly into the steering wheel of the vehicle, allowing for convenient and accurate monitoring of the driver's pulse without the need for wearable devices or constant contact with the steering wheel. Furthermore, the computer system in the vehicle is configured to diagnose whether the driver is experiencing a pulseless condition and provide immediate notification and instructions for seeking medical assistance, enhancing driver safety and potentially saving lives.

SUMMARY OF THE INVENTION

Disclosed is a method for using a PPG sensor as a diagnostic and safety aid for vehicular drivers while the vehicle is in motion. PPG is a very reliable method for monitoring a person's arteriolo-capillary pulse wave intervals or heartbeat frequency.

The term "pulseless condition" is defined as any time interval between heart beats in excess of a first pre-determined time interval. This first pre-determined time interval is preferably three seconds which coincides with the American Heart Association (AHA) recommendation for pacemaker implantation.

The invention can be used not only to monitor the heart condition of the driver, but can also be utilized to control activities of the vehicle after a pulseless condition has been diagnosed for the driver by the on-board computer.

For example, after a driver has been diagnosed with a pulseless condition over the first pre-determined time interval, such as over three seconds, the on-board computer can alert the driver of his condition. This alert can take the form of audio, visual or both. An audio alert can inform the driver to proceed to a medical facility for evaluation. The on-board computer can calculate the driving directions based on GPS position of the vehicle in relation to a nearby medical facility. Audio can be used to provide step-by-step directions.

However, if the driver's pulseless condition worsens in which the time interval between heart beats exceeds a second pre-determined time interval that is indicative of the driver about to lose consciousness, such as about six seconds, individuals following immediately behind the driver or those in oncoming traffic are in danger because they are traveling in close proximity to a driver about to lose control of his vehicle. As a warning to those individuals, the on-board computer after diagnosing a pulseless condition exceeding the second pre-determined time interval, for example, can be programmed to activate the front lights and/or rear tail lights in a specific pattern which can alert individuals in close proximity of a problem with the driver of that vehicle. In addition, if the driver becomes incapacitated, the on-board computer can take control of the vehicle and perform steps necessary to maneuver and safely bring the vehicle to a stop on the side of the road.

Additionally, if the vehicle is properly equipped, an inhalant adrenergic vapor may be released to the driver and can be programmed for discharge after the first pre-determined time interval, second pre-determined time interval, or at some other time.

My method and system provides for the safety of individuals, including the driver who may experience a pulseless condition.

In one embodiment of use of my system, a vehicle is provided to perform the functions required by the invention. Such a vehicle would have GPS navigation, a video display, a proximity sensor system that is used for collision avoidance and may incorporate multiple cameras around the periphery of the vehicle; all of which are operably connected to the on-board computer which is also connected to alert mechanisms such as the vehicle lights, sound system and possibly a system for release of medication to the driver.

Besides having the aforementioned equipment, the vehicle would further be equipped with at least one PPG sensor for monitoring the arteriolo-capillary pulse wave intervals of the driver. In a preferred embodiment, the at least one PPG sensor is positioned on or around the steering wheel and is also operably connected to the on-board computer. The at least one PPG sensor is positioned on areas of the steering wheel most likely to be gripped by the driver. Preferably, the at least one PPG sensor is positioned circumferentially about the steering wheel. Because different drivers can grip the steering wheel differently, the at least one PPG sensor should be located on those areas of the steering wheel typically gripped by the driver.

The vehicle's computer would be programmed to process arteriolo-capillary pulse wave intervals received from the at least one PPG sensor and determine whether the driver is experiencing pulseless condition.

Where the at least one PPG sensor is part of the steering wheel, it is necessary that the driver have at least one hand on the steering wheel positioned to be in contact with the PPG sensor while driving. To ensure the driver maintains at least one hand on the steering wheel, an audible sound or visual signal may activate before the first pre-determined time interval occurs as a warning to the driver to place a hand on the wheel to prevent a false diagnosis of a pulseless condition.

In one embodiment of my method, once a pulseless condition is diagnosed by the on-board computer represented as the first pre-determined time interval, the computer can initiate one or more of the following: a) inform the driver of his cardiac condition and recommend traveling to the nearest medical facility for evaluation; or b) provide directions to a nearby medical facility based on the GPS location relative to the vehicle. In a preferred embodiment, the vehicle display can be a heads-up-display (HUD) which would show a message to suggest placing both hands on the steering wheel while driving, to be able to obtain more reliable heart information so that real-time arteriolo-capillary pulse wave intervals and possibly an optional sensor capable of being used to generate an ECG rhythm strip in which both sets of data can be wirelessly transmitted by the vehicle to a medical facility.

If the driver's condition worsens to having a pulseless condition exceeding the second pre-determined time interval, my invention can include at least one selected from the group consisting of: c) the on-board computer will activate the lights of the vehicle (such as the front lights, cabin lights, rear tail lights or a combination thereof) in such a way to alert drivers behind and in close proximity of the condition of the driver of the vehicle; d) take over control of the vehicle to safely maneuver and slow the vehicle until a safe destination is reached; and e) if the vehicle is equipped, dispensing an inhalant medication within the vehicle cabin to reverse the pulseless condition of the driver.

The medication described in e) for example, can be a cannister or capsule containing an ammonia inhalant that can be installed within the vehicle cabin; such as on the center of steering wheel. A mechanism would be provided to either release the ammonia vapor from the cannister or to crush the ammonia inhalant capsule. Either mechanism would be operably coupled to the on-board computer. The release of ammonia vapor into the vehicle cabin directly in front of the driver's nose, would cause an olfactory unconditional adrenergic reflex that would be triggered to prevent full loss of consciousness.

Also, it is possible that after diagnosis of a pulseless condition, the driver will regain pulse spontaneously. In this case, the on-board computer can be programmed to discontinue the steps described earlier.

As used in the claims, the first pre-determined time interval is between 3.0-3.5 seconds. The second pre-determined time interval is between 6.0-7.5 seconds.

Alternative methods can be designed. For example, a first alternative method can be designed to only assume functions in the vehicle when the driver is likely experiencing a critical medical condition such as loss of consciousness. This first alternative method would assume vehicle function when the computer determines the interval between consecutive heart beats of the driver and whether the interval between heartbeats exceed a pre-determined time interval of between 6.0-7.5 seconds. If this pre-determined time interval is exceeded, the computer will perform at least one selected from the group consisting of: i) the on-board computer will activate the lights of the vehicle to alert drivers behind and in close proximity, of the condition of the driver of the vehicle; ii) assume control of the vehicle and safely maneuver the vehicle until a safe destination is reached; and, iii) if the vehicle is equipped with an inhalant medication for dispensing to the driver, dispensing the inhalant medication.

For a second alternative embodiment in which the computer determines whether the interval between heart beats exceed a pre-determined time interval of between 6.0-7.5 seconds, the computer will perform at least one action selected from the group consisting of: activating the lights of the vehicle, primarily the rear tail lights, and maneuver the vehicle safely to a controlled stop. Also, the computer further determines whether the interval between consecutive heart beats of the driver exceed 7.0 seconds, the computer will cause the inhalant medication to be discharged.

DETAILED DESCRIPTION OF THE PREFERRED EMBODIMENT

The figures presented herein are for illustrative purposes and are not necessarily shown in correct proportion or scale.

Figure 1:
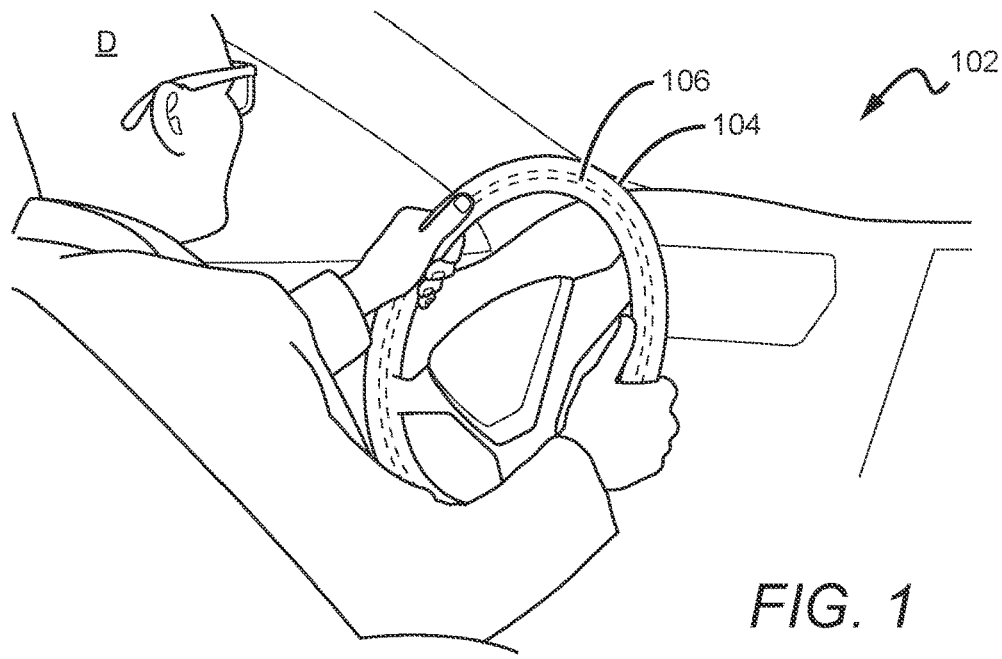
FIG. 1 is a view of a driver in a vehicle cabin having hands positioned about a steering wheel adapted with a heart rate sensor.

FIG. 1 illustrates the general position of a driver D seated within the vehicle cabin of a vehicle 102 while driving. Vehicle 102 has a proximity sensor system (not shown) that includes collision avoidance hardware, lane departure solutions and cameras. These systems as well as the vehicle lights (not shown), a video display (not shown) and sound system (not shown) are operably connected to an on-board computer of the vehicle.

Steering wheel 104 is adapted to include at least one sensor 106 as shown in broken line positioned circumferentially for communicating heart beat information with the on-board computer. Sensor 106 is preferably a photoplethysmography sensor and is designed so it will function if contacted by one of the driver's hands. Depending on the design of the steering wheel, it may be necessary for more than one sensor to be located on steering wheel 104 so that gripping the steering wheel with one hand anywhere on the steering wheel will activate sensor 106.

Figure 2:
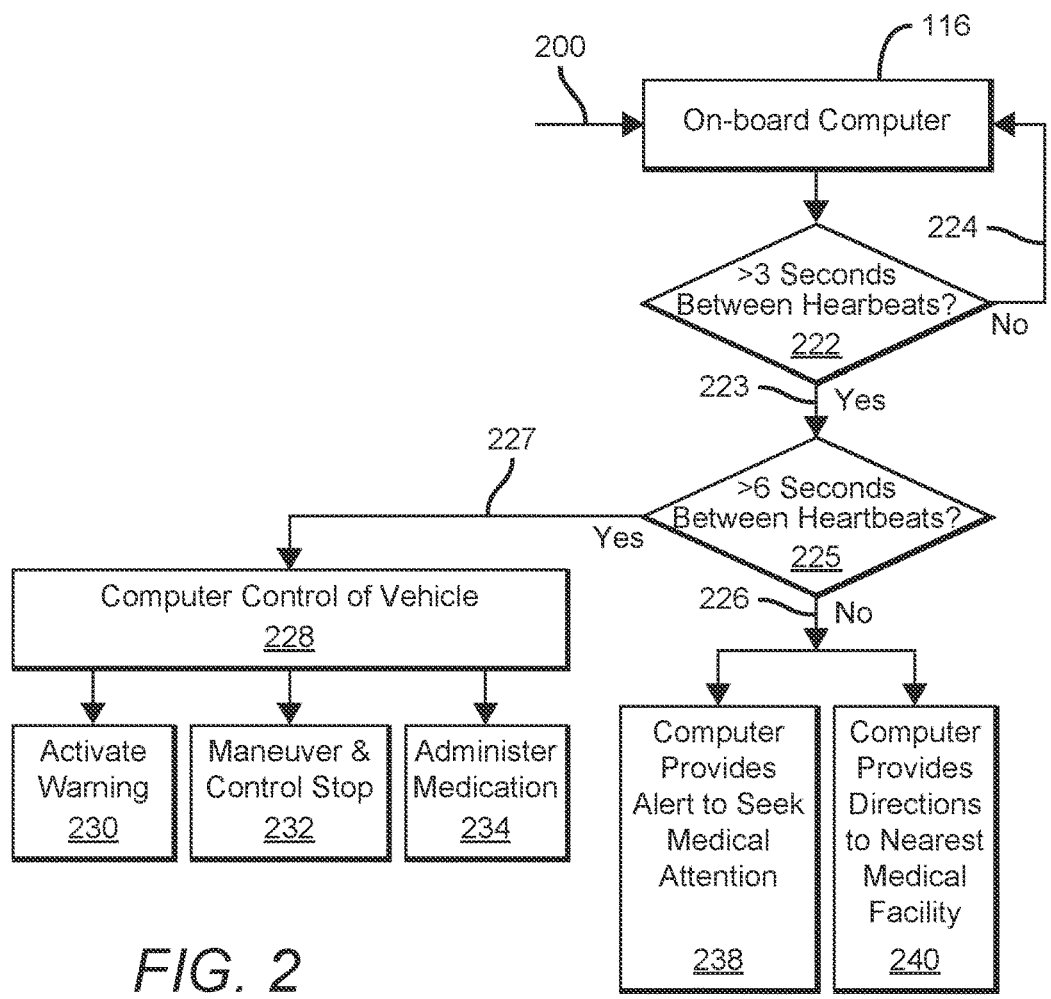
FIG. 2 is a diagram illustrating the computer decision sequence in response to the data received from the heart rate sensor.

Sensor 106 is connected to the on-board computer 116. While vehicles may have more than one computer, reference made to a computer is representative of the overall decision making process. FIG. 2 illustrates a flow diagram related to the functionality of computer 116 based on data received from sensor 106 and a method of use.

While driver D grips steering wheel 104, sensor 106 measures each consecutive arteriolo-capillary pulse wave intervals and the data is transmitted to computer 116 (step 200) and specifically, the time interval between each heart beat of the driver. Computer 116 determines if the time interval between the driver's arteriolo-capillary pulse wave intervals exceed a first pre-determined time interval which, in this example is set to 3.0 seconds (step 222) and is indicative of the driver experiencing a pulseless condition. If no (step 224), computer 116 will continue to monitor. However, if the time interval between arteriolo-capillary pulse wave intervals is greater than 3.0 seconds (step 223), computer 116 next determines the severity of the pulseless condition, by determining if the time interval between the driver's arteriolo-capillary pulse wave intervals exceed a second pre-determined time interval of six seconds (step 225).

To eliminate false positives, which will occur if the driver does not have either hand on steering wheel 104 for more than three seconds, computer 116 can sense whether sensor 106 is not in contact with the driver's hand or can monitor the facial expression of the driver if a camera facing the driver is installed. If no contact is determined for a period such as two seconds, a warning will be communicated to the driver, either an audible or visual, to instruct the driver to place his hands back on steering wheel 104 and contact with sensor 106.

The computer determines whether the pulseless condition exceeds a second pre-determined time interval of between 6.0-7.5 seconds, which in this example, is set to 6.0 seconds (step 225). If no (step 226), the computer will provide an alert (step 238). The alert can use the audio system to inform the driver of his condition and to seek medical attention or, the alert can be provided on a visual display screen or heads-up display if the vehicle is so equipped; or both audio and display. If the vehicle includes a navigation system, then the computer using mobile GPS location, can plot the direction to the nearest medical facility and provide directions to the driver (step 240).

If the computer determines a pulseless condition which exceeds the second pre-determined time interval, in this example set to 6.0 seconds (step 227), the computer will assume control of the vehicle (step 228) because of the driver's imminent loss of consciousness.

The function of computer 116 when a pulseless condition exceeds the predetermined time interval of 6.0 seconds is to alert individuals nearby of the condition of the driver and to take over control of the vehicle to stop the vehicle in the safest manner possible taking into account the surrounding traffic environment. For example, if the vehicle is traveling on a freeway and a pulseless condition exceeding 6.0 seconds is determined by computer 116 (step 225), using the exterior sensors (not shown) positioned around vehicle 102, computer 116 will assume control of the vehicle (step 228) and activate a warning such as the rear tail lights in a pattern to alert individuals traveling behind of the condition of the driver (step 230). Computer 116 also assumes control of the vehicle using the vehicle's proximity sensor system and cameras, and will plot and execute a safe course, taking into account the proximity of other vehicles, to bring the vehicle to a stop on the side of the road (step 232).

Optionally, vehicle 102 can also be equipped for the discharge of an inhalant medication for inhalation by the driver (step 234). In the situation where a pulseless condition exceeding about six seconds is diagnosed, computer 116 can administer medication such as the release a volume of an inhalant such as ammonia vapor within the vehicle to cause an olfactory unconditional adrenergic reflex and prevent full loss of consciousness.

Figure 3:
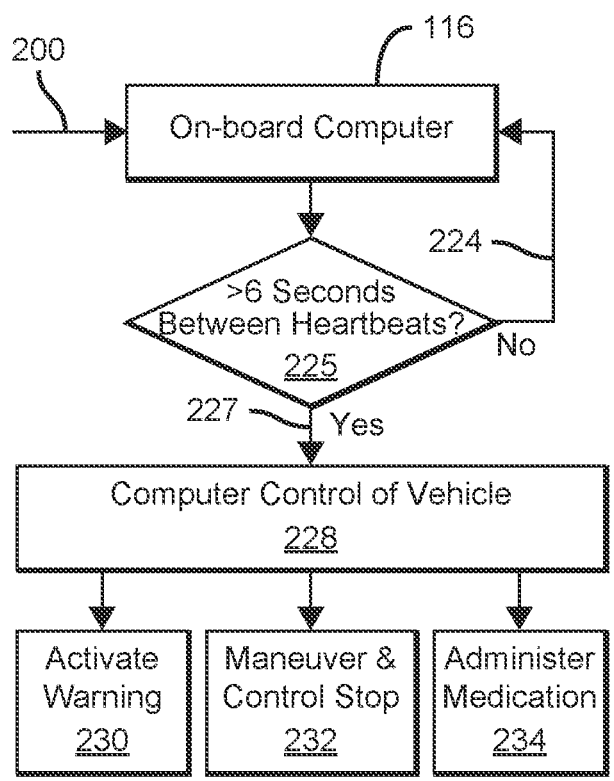
FIG. 3 is a diagram of a first alternative method illustrating the computer decision sequence in response to the data received from the heart rate sensor.

FIG. 3 illustrates the flow diagram of a first alternative method related to the functionality of computer 116 based on data received from sensor 106 and a method of use.

Data is transmitted to computer 116 (step 200) as described earlier. Computer 116 determines whether the interval between heartbeats of the driver exceeds a pre-determined time interval of between 6.0-7.5 seconds, in this example 6.0 seconds (step 225). If no (step 224), computer 116 will continue to monitor. However, if the detectable interval between heartbeats of the driver is greater than the pre-determined time interval (step 227), computer 116 will assume control of the vehicle (step 228) and perform at least one of the following actions: activating warning lights such as the rear tail lights (step 230); maneuvering the vehicle safely to a controlled stop (step 232); and, if the vehicle is equipped with inhalant medication, discharging an inhalant medication to treat the driver (step 234).

In another embodiment, if the detectable interval between heartbeats of the driver is greater than the pre-determined time interval (step 227) which is between 6.0 and 7.0 seconds, computer 116 will assume control of the vehicle (step 228) and perform at least one of the following actions: activating warning lights such as the rear tail lights (step 230); and, maneuvering the vehicle safely to a controlled stop (step 232). If the vehicle is equipped with inhalant medication, the computer can be programmed to discharge an inhalant medication to treat the driver (step 234) if the time interval between the driver's heart beats exceeds a different threshold, by way of example, exceeding 7.0 seconds.

In some aspects, the techniques described herein relate to a vehicle with a computer configured to diagnose whether a driver of a vehicle is experiencing a pulseless condition including: a steering wheel adapted to include at least one photoplethysmography sensor located circumferentially on the steering wheel to communicate to the computer, heart beats of the driver when the steering wheel is gripped by the driver, a proximity sensor system, a visual display, front lights, cabin lights, rear tail lights, navigation system and an audio system, wherein the steering wheel, at least one sensor, proximity sensor system, front lights, cabin lights, rear tail lights and audio system are each operably connected to the computer; and, the computer determines the interval between consecutive heart beats of the driver and whether the interval between heart beats exceed a pre-determined time interval of between 6.0-7.5 seconds, and if exceeded, the computer will perform at least one action selected from the group consisting of: activating one or more of the front lights, cabin lights and rear tail lights of the vehicle; and, maneuvering the vehicle safely to a controlled stop.

In some aspects, the techniques described herein relate to a vehicle with a computer configured to diagnose whether a driver of a vehicle is experiencing a pulseless condition including: a steering wheel adapted to include at least one photoplethysmography sensor located circumferentially on the steering wheel to communicate to the computer, heart beats of the driver when the steering wheel is gripped by the driver, a proximity sensor system, a visual display, rear tail lights, an inhalant medication mounted for discharge within the vehicle in sufficient proximity to be inhaled by the driver, navigation system and an audio system, wherein the steering wheel, at least one sensor, proximity sensor system, rear tail lights, discharge of inhalant medication and audio system are each operably connected to the computer; and, the computer determines the interval between consecutive heart beats of the driver and whether the interval between heart beats exceed a pre-determined time interval of between 6.0-7.0 seconds, and if exceeded, the computer will perform at least one action selected from the group consisting of: activating the rear tail lights and maneuvering the vehicle safely to a controlled stop.

In some aspects, the techniques described herein relate to a vehicle in which the computer further determines whether the interval between consecutive heart beats of the driver exceed 7.0 seconds, and if exceeded, the computer will cause the inhalant medication to be discharged.

The invention claimed is:

1. A vehicle with a computer configured to diagnose whether a driver of a vehicle is experiencing a pulseless condition comprising:

a steering wheel adapted to include at least one photoplethysmography sensor located circumferentially on the steering wheel to communicate to the computer, heart beats of the driver when the steering wheel is gripped by the driver, a proximity sensor system, a visual display, front lights, cabin lights, rear tail lights, navigation system and an audio system, wherein the steering wheel, at least one sensor, proximity sensor system, front lights, cabin lights, rear tail lights and audio system are each operably connected to the computer; and, the computer determines the interval between consecutive heart beats of the driver and whether the interval between heart beats exceed a pre-determined time interval of between 6.0-7.5 seconds, and if exceeded, the computer will perform at least one action selected from the group consisting of: activating one or more of the front lights, cabin lights and rear tail lights of the vehicle; and, maneuvering the vehicle safely to a controlled stop.

2. A vehicle with a computer configured to diagnose whether a driver of a vehicle is experiencing a pulseless condition comprising:

a steering wheel adapted to include at least one photoplethysmography sensor located circumferentially on the steering wheel to communicate to the computer, heart beats of the driver when the steering wheel is gripped by the driver, a proximity sensor system, a visual display, rear tail lights, an inhalant medication mounted for discharge within the vehicle in sufficient proximity to be inhaled by the driver, navigation system and an audio system, wherein the steering wheel, at least one sensor, proximity sensor system, rear tail lights, discharge of inhalant medication and audio system are each operably connected to the computer; and, the computer determines the interval between consecutive heart beats of the driver and whether the interval between heart beats exceed a pre-determined time interval of between 6.0-7.0 seconds, and if exceeded, the computer will perform at least one action selected from the group consisting of: activating the rear tail lights and maneuvering the vehicle safely to a controlled stop.

3. The vehicle of claim 2 in which the computer further determines whether the interval between consecutive heart beats of the driver exceed 7.0 seconds, and if exceeded, the computer will cause the inhalant medication to be discharged.

* * * * *